United States Patent [19]

Rodewald et al.

[11] Patent Number: 4,665,264

[45] Date of Patent: May 12, 1987

[54] CATALYTIC CONVERSION

[75] Inventors: Paul G. Rodewald, Rocky Hill, N.J.; Ernest W. Valyocsik, Yardley, Pa.

[73] Assignee: Mobil Oil Corporation, New York, N.Y.

[21] Appl. No.: 861,790

[22] Filed: May 9, 1986

Related U.S. Application Data

[63] Continuation-in-part of Ser. No. 705,821, Feb. 26, 1985, abandoned.

[51] Int. Cl.$^4$ .............. C07C 2/02; C07C 2/58; C07C 2/52
[52] U.S. Cl. .................. 585/533; 585/722; 585/418; 585/419; 585/420
[58] Field of Search .............. 585/533, 722, 418, 419, 585/420

[56] References Cited

U.S. PATENT DOCUMENTS

| | | | |
|---|---|---|---|
| 3,702,886 | 11/1972 | Arqauer et al. | 423/328 |
| 3,917,738 | 11/1975 | Fenske et al. | 585/722 |
| 3,960,978 | 6/1976 | Givens et al. | 260/683.15 R |
| 4,021,502 | 5/1977 | Plank et al. | 260/683.15 R |
| 4,100,218 | 7/1978 | Chen et al. | 260/673 |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,287,166 | 9/1981 | Dwyer et al. | 423/328 |
| 4,350,835 | 9/1982 | Chester et al. | 585/415 |
| 4,427,787 | 1/1984 | Miale et al. | 502/71 |
| 4,483,835 | 11/1984 | Zones | 423/328 |
| 4,547,612 | 10/1985 | Tabak | 585/533 |
| 4,547,613 | 10/1985 | Garwood et al. | 585/533 |
| 4,554,396 | 11/1985 | Chang et al. | 585/531 |

*Primary Examiner*—Curtis R. Davis
*Attorney, Agent, or Firm*—Alexander J. McKillop; Michael G. Gilman; Dennis P. Santini

[57] ABSTRACT

A process is provided for converting feedstock comprising $C_2+$ olefins, $C_2$–$C_7$ paraffins or mixtures thereof to product comprising $C_5+$ hydrocarbons over a catalyst comprising zeolite ZSM-58.

24 Claims, No Drawings

CATALYTIC CONVERSION

CROSS-REFERENCE TO RELATED APPLICATION

This application is a continuation-in-part of application Ser. No. 705,821, filed Feb. 26, 1985 and now abandoned.

BACKGROUND OF THE INVENTION

1. Field of the Invention

This invention relates to a process for conversion of feedstock comprising $C_2+$ olefins, $C_2-C_7$ paraffins or mixtures thereof to product comprising $C_5+$ hydrocarbons. The process comprises contacting, under conversion conditions, said feedstock with a catalyst comprising a synthetic, thermally stable, molecular shape selective, active form of crystalline material designated ZSM-58.

2. Description of Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cationl. This can be expressed wherein the ratio of aluminum to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by convenient symbols, as illustrated by zeolite ZSM-5 (U.S. Pat. No. 3,702,886).

The use of certain zeolites as catalyst components is taught in U.S. Pat. No. 4,305,808, for example.

The silica-to-alumina ratio of a given zeolite is often variable; for example, zeolite X (U.S. Pat. No. 2,882,244) can be synthesized with a silica-to-alumina ratio of from 2 to 3; zeolite Y (U.S. Pat. No. 3,130,007) from 3 to about 6. In some zeolites, the upper limit of silica-to-alumina ratio is virtually unbounded. Zeolite ZSM-5 is one such material wherein the silica-to-alumina ratio is at least 5. U.S. Pat. No. 3,941,871 discloses a crystalline metal organo silicate essentially free of aluminum and exhibiting an x-ray diffraction pattern characteristic of ZSM-5 type aluminosilicate. U.S. Pat. Nos. 4,061,724; 4,073,865 and 4,104,294 describe microporous crystalline silicas or organo silicates wherein the aluminum content present is at impurity levels.

U.S. Pat. Nos. 3,960,978 and 4,021,502, disclose conversion of $C_2-C_5$ olefins, alone or in admixture with paraffinic components, into higher hydrocarbons over crystalline zeolites having controlled acidity. U.S. Pat. Nos. 4,150,062, 4,211,640 and 4,227,992 teach processing techniques for conversion of olefins to gasoline and distillate. U.S. Pat. No. 4,504,691 teaches a multi-step process for converting olefinic feedstock comprising ethylene and $C_3+$ olefins to heavier liquid hydrocarbon product. The above identified disclosures are incorporated herein by reference.

Olefinic feedstocks may be obtained from various sources, including fossil fuel processing streams, such as gas separation units, cracking of $C_2°$ hydrocarbons, coal byproducts, and various synthetic fuel processing streams. Cracking of ethane and conversion of conversion effluent is disclosed in U.S. Pat. No. 4,100,218 and conversion of ethane to aromatics over Ga-ZSM-5 is disclosed in U.S. Pat. No. 4,350,835. Olefinic effluent from fluidized catalytic cracking of gas oil or the like is a valuable source of olefins, mainly $C_3-C_4$ olefins.

SUMMARY OF THE INVENTION

The present invention relates to a novel process for converting feedstock comprising $C_2+$ olefins, $C_2-C_7$ paraffins or a mixture thereof to product comprising $C_5+$ hydrocarbons over a catalyst comprising zeolite ZSM-58.

DESCRIPTION OF SPECIFIC EMBODIMENTS

The contents of application Ser. No. 705,821, filed Feb. 26, 1985, are entirely incorporated herein by reference.

The feedstock to the present process comprises $C_2-C_7$ paraffins and/or olefins of at least two carbon atoms. Product of the present process comprises $C_5+$ hydrocarbons. When the feedstock comprises paraffins, product comprises aromatics, e.g., benzene, toluene and xylenes, and conversion conditions include a temperature of from about 100° C. to about 700° C., a pressure of from about 10 kPa to about 11,000 kPa, preferably from 10 kPa to 7000 kPa, a liquid hourly space velocity (LHSV) of from about 0.1 $hr^{-1}$ to about 500 $hr^{-1}$, preferably from 0.5 $hr^{-1}$ to 400 $hr^{-1}$, and a hydrogen/hydrocarbon mole ratio of from 0 (no added hydrogen) to about 20. Under these same conversion conditions, a feedstock comprising $C_2-C_7$ olefins is converted to product comprising aromatics, e.g., benzene, toluene and xylenes.

A feedstock to the present process may comprise primarily $C_2-C_7$ olefins for conversion to gasoline and distillate products when the conversion conditions are tailored to be within the following ranges. In general, the temperature will be maintained at from about 190° C. to about 375° C., the pressure at from about 400 kPa to about 11,000 kPa, preferably from 400 kPa to about 7000 kPa, and the liquid hourly space velocity (LHSV based on feedstock olefin) at from about 0.3 to about 2, preferably from 0.5 to 2 $hr^{-1}$. Specifically when the present process is operated in the distillate mode, the temperature will be from about 190° C. to about 315° C., the pressure from about 4200 kPa to about 11,000 kPa, preferably from 4200 kPa to 7000 kPa, and the LHSV from about 0.3 to about 1.0 hr$^{-1}$, preferably from 0.5 to 1.0 hr$^{-1}$. When the present process is operated in the gasoline mode, the temperature will be from about 230° C. to about 375° C., the pressure from about 400 kPa to about 4700 kPa, preferably from 400 kPa to 3000 kPa and the LHSV from about 0.3 to about 2.0, preferably from 0.5 to 2.0 hr$^{-1}$. The feedstocks, products, process conditions and other variables for conversion of olefins to higher hydrocarbons are detailed in U.S. Pat. No. 4,456,778, incorporated entirely herein by reference.

The present process requires a catalyst comprising the synthetic, thermally stable, molecular shape selective crystalline ZSM-58.

The structure of ZSM-58 is distinguished from other crystalline silicates by a unique X-ray diffraction pattern. The typical X-ray diffraction pattern intensities for ZSM-58 are shown in Table 1, hereinafter.

The crystalline silicate ZSM-58 has a composition involving silica and alumina in the relationship $$(0.1-2)Al_2O_3:(100)SiO_2.$$

In the as-synthesized form, ZSM-58 has a formula, on an anhydrous basis and in terms of moles of oxides per 100 moles of silica, as follows:

$$(0.1-2.0)R_2O:(0.02-1.0)M_{2/n}O:(0.1-2)Al_2O_3:(100)SiO_2$$

wherein M is an alkali or alkaline earth metal cation, n is the valence of M, and R is an organic cation.

TABLE 1

| Interplanar d-Spacing (A) | | Relative Intensity, I/Io |
|---|---|---|
| 13.70 | ±0.20 | W |
| 11.53 | ±0.20 | W-VS |
| 10.38 | ±0.20 | W |
| 7.82 | ±0.14 | W-VS |
| 6.93–6.79 | ±0.14 | W-VS |
| 6.19 | ±0.14 | W-VS |
| 5.94 | ±0.12 | W-M |
| 5.77 | ±0.12 | VS |
| 5.22 | ±0.12 | W |
| 5.18 | ±0.10 | VS |
| 4.86 | ±0.09 | M-S |
| 4.72 | ±0.08 | S |
| 4.57 | ±0.08 | W |
| 4.51 | ±0.08 | S |
| 4.43 | ±0.08 | W |
| 4.19 | ±0.08 | W |
| 4.15 | ±0.08 | M |
| 4.00 | ±0.07 | W |
| 3.97 | ±0.07 | W |
| 3.89 | ±0.07 | W |
| 3.84 | ±0.07 | M |
| 3.81 | ±0.07 | W-M |
| 3.59 | ±0.06 | W |
| 3.46 | ±0.06 | W-M |
| 3.41 | ±0.06 | S-VS |
| 3.36 | ±0.06 | S-VS |
| 3.32 | ±0.06 | M-S |
| 3.29 | ±0.05 | W |
| 3.17 | ±0.05 | W-M |
| 3.07 | ±0.05 | W-M |
| 3.05 | ±0.05 | W-M |
| 3.01 | ±0.05 | W-M |
| 2.88 | ±0.05 | W |
| 2.85 | ±0.05 | W |
| 2.75 | ±0.05 | W |
| 2.67 | ±0.04 | W |
| 2.60 | ±0.04 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 I/I$_o$, where I$_o$ is the intensity of the strongest line or peak, and d (obs.) the interplanar spacing in Angstrom Units (A), corresponding to the recorded lines, were determined. In Table 1, the relative intensities are given in terms of the symbols W=weak, M=medium, S=strong and VS=very strong. In terms of intensities, these may be generally designated as follows:

W=0–20
M=20–40
S=40–60
VS=60–100

It should be understood that this X-ray diffraction pattern is characteristic of all the species of ZSM-58 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment. Multiplets may be observed in the typical X-ray pattern for ZSM-58 at d-spacing values of 6.93–6.79±0.14, 4.86±0.09, 3.41±0.06, 3.07±0.05 and 3.01±0.05 Angstroms.

The original alkali or alkaline earth metal cations of the as synthesized ZSM-58 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-58 more catalytically active for the present reaction. These include hydrogen, rare earth metals and metals of Groups IIA, IIIA, IVA, IB, IIB, IIIB, IVB, VIB and VIII of the Periodic Table of the Elements.

Typical ion exchange technique would be to contact the synthetic ZSM-58 with a salt of the desired replacing cation or cations. Examples of such salts include the halides, e.g. chlorides, nitrates and sulfates.

The crystalline silicate ZSM-58 can also be used in the present process in intimate combination with a hydrogenating component such as tungsten, vanadium, molybdenum, rhenium, nickel, cobalt, chromium, manganese, or a noble metal such as platinum. Such component can be exchanged into the composition to the extent aluminum is in the structure, impregnated therein or intimately physically admixed therewith. Such component can be impregnated in or on to it such as for example, by, in the case of platinum, treating the ZSM-58 with a solution containing a platinum metal-containing ion. Thus, suitable platinum compounds include chloroplatinic acid, platinous chloride and various compounds containing the platinum amine complex.

The crystalline silicate ZSM-58, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

The ZSM-58 should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-58 in a vacuum, but a longer time is required to obtain a sufficient amount of dehydration.

The ZSM-58 can be prepared from a reaction mixture containing sources of an alkali or alkaline earth metal (M) cation, an oxide of aluminum, an oxide of silicon, an organic cation (R) of a methyltropinium salt, e.g. halide, hydroxide, sulfate, etc., and water, said reaction mixture having a composition, in terms of mole ratios of oxides, within the following ranges:

| Reactants | Useful | Preferred |
|---|---|---|
| $SiO_2/Al_2O_3$ | 50–1000 | 70–500 |
| $H_2O/SiO_2$ | 5–200 | 10–100 |
| $OH^-/SiO_2$ | 0–2.0 | 0.10–1.0 |
| $M/SiO_2$ | 0.01–3.0 | 0.10–1.0 |
| $R/SiO_2$ | 0.01–2.0 | 0.10–0.50 | wherein R and M are as above defined.

Crystallization of the ZSM-58 can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered. The reaction mixture can be prepared utilizing materials which supply the appropriate oxides. Such materials may include sodium silicate, silica hydrosol, silica gel, silicic acid, sodium hydroxide, a source of aluminum, and the methyltropinium salt directing agent. The methyltropinium salt may be synthesized by selective methylation of 3-tropanol at the bridgehead nitrogen. This salt has the following formula:

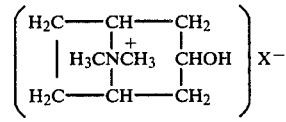

wherein X is an anion, such as, for example, a halide (e.g. iodide, chloride or bromide), nitrate, hydroxide, sulfate, bisulfate, perchlorate, etc. U.S. application Ser. No. 705,820, filed Feb. 26, 1985 teaches these salts and their synthesis and is incorporated herein by reference.

It should be realized that the reaction mixture oxides can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the ZSM-58 crystals is facilitated by the presence of at least 0.01 percent, preferably 0.10 percent and still more preferably 1 percent, seed crystals (based on total weight) of crystalline product.

The crystals prepared as above can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In practicing the desired chemical conversion process, it may be useful to composite the crystalline zeolite ZSM-58 with matrix-comprising material resistant to the temperature and other conditions employed in the process. Such matrix material is useful as a binder and imparts additional resistance to the catalyst for the temperature, pressure and reactant feed stream velocity conditions allowed in the present process. The composite may be in the form of an extrudate.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families which include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing matrix materials, the catalyst employed herein may be composited with a porous matrix material such as alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of activity enhanced zeolite component and matrix, on an anhydrous basis, may vary widely with the zeolite content of the dry composite ranging from about 1 to about 99 percent by weight and more usually in the range of about 5 to about 80 percent by weight.

In order to more fully illustrate the nature of the invention and the manner of practicing same, the following examples are presented. In the examples, whenever sorption data are set forth for comparison of sorptive capacities for cyclohexane and/or n-hexane, they were measured on an electrobalance as follows:

The adsorbate was activated at 500° C. in flowing helium until at constant weight. Adsorptions were conducted at 90° C., with the hydrocarbon containing helium gas stream flowing around the the sample. Partial presssures of hexane and cyclohexane were 28 and 35 torr, respectively. The measurements were continued until the sample reached constant weight. The increase in weight was converted to adsorption capacity of the sample in g/100 g of activated zeolite.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. IV, pp. 527–529 (August 1965), each incorporated herein as to that description. The relationship of Alpha Value to the intrinsic rate constants for many acid-catalyzed reactions, such as that of the present invention, is detailed in "The Active Site of Acidic Aluminosilicate Catalysts," *Nature*, Vol. 309, No. 5969, pp. 589–591, 14 June 1984, incorporated herein by reference as to that detail.

EXAMPLES 1-6

Six separate synthesis reaction mixtures were prepared with compositions indicated in Table 2. The mixtures were prepared with silica sol (30 percent SiO$_2$), NaAlO$_2$, NaOH, a methyltropinium salt, i.e. iodide, and water. The mixtures were maintained at 160° C. for 4 days in a stainless steel, stirred (400 rpm) autoclave at autogenous pressure. Solids were separated from any unreacted components by filtration and then water washed, followed by drying at 110° C. The product crystals were analyzed by X-ray diffraction and chemical analysis. The product of Example 1 was found to be crystalline ZSM-58 with a trace of unidentified second component impurity. The products from Examples 2-6 proved to be 100 percent crystalline ZSM-58.

The X-ray diffraction pattern of the Example 4 crystals, after calcination at 538° C. for 17 hours in air, is set forth as illustration in Table 3. Other properties of each crystalline product are presented in Table 4. In the latter table, compositions are calculated on the basis of 100 (SiO$_2$+AlO$_2$$^-$) tetrahedra. The as-synthesized ZSM-58 from these examples contains from 3.8 to 5.0 methyltropinium cations per 100 tetrahedra.

TABLE 2

| | Mixture Composition (mole ratios) | | | | |
|---|---|---|---|---|---|
| Example | $\frac{SiO_2}{Al_2O_3}$ | $\frac{H_2O}{SiO_2}$ | $\frac{OH^-}{SiO_2}$ | $\frac{Na^+}{SiO_2}$ | $\frac{R^*}{SiO_2}$ |
| 1 | 300 | 40 | 0.30 | 0.31 | 0.25 |
| 2 | 200 | 40 | 0.30 | 0.31 | 0.25 |
| 3 | 90 | 40 | 0.40 | 0.42 | 0.25 |
| 4 | 90 | 40 | 0.30 | 0.32 | 0.25 |
| 5 | 90 | 40 | 0.30 | 0.32 | 0.25 |
| 6 | 70 | 40 | 0.30 | 0.33 | 0.25 |

*R = methyltropinium cation.

TABLE 3

| d(A) | Observed 2 Theta | Relative Intensity |
|---|---|---|
| 13.57 | 6.511 | 7.4 |
| 11.44 | 7.721 | 51.2 |
| 10.29 | 8.588 | 4.1 |

TABLE 3-continued

| d(A) | Observed 2 Theta | Relative Intensity |
|---|---|---|
| 7.76 | 11.389 | 53.6 |
| 6.89 | 12.834 | 60.1 |
| 6.84 | 12.932 | 33.0 |
| 6.15 | 14.378 | 57.8 |
| 5.91 | 14.987 | 19.5 |
| 5.74 | 15.435 | 85.8 |
| 5.16 | 17.173 | 100.0 |
| 4.84 | 18.317 | 51.9 |
| 4.70 | 18.865 | 56.0 |
| 4.52 | 19.612 | 20.3 |
| 4.49 | 19.755 | 51.7 |
| 4.41 | 20.093 | 4.7 |
| 4.13 | 21.486 | 26.0 |
| 3.98 | 22.307 | 11.8 |
| 3.96 | 22.404 | 8.9 |
| 3.87 | 22.969 | 17.1 |
| 3.82 | 23.268 | 30.6 |
| 3.80 | 23.365 | 25.6 |
| 3.57 | 24.882 | 16.2 |
| 3.44 | 25.849 | 35.2 |
| 3.38 | 26.303 | 96.5 |
| 3.35 | 26.546 | 86.7 |
| 3.34 | 26.619 | 80.8 |
| 3.30 | 26.947 | 66.2 |
| 3.28 | 27.158 | 9.1 |
| 3.16 | 28.237 | 23.3 |
| 3.06 | 29.159 | 26.8 |
| 3.06 | 29.176 | 31.2 |
| 3.03 | 29.406 | 22.7 |
| 2.996 | 29.816 | 25.2 |
| 2.988 | 29.901 | 21.2 |
| 2.870 | 31.158 | 4.1 |
| 2.842 | 31.473 | 5.1 |
| 2.664 | 33.638 | 5.5 |
| 2.589 | 34.643 | 4.8 |
| 2.503 | 35.869 | 4.3 |
| 2.488 | 36.099 | 6.3 |
| 2.438 | 36.863 | 9.0 |
| 2.421 | 37.134 | 14.9 |
| 2.390 | 37.626 | 5.8 |
| 2.354 | 38.230 | 2.8 |
| 2.332 | 38.591 | 4.3 |
| 2.300 | 39.161 | 16.7 |
| 2.236 | 40.319 | 2.4 |
| 2.231 | 40.413 | 1.9 |
| 2.211 | 40.807 | 3.2 |
| 2.164 | 41.739 | 1.7 |
| 2.111 | 42.836 | 1.4 |
| 2.073 | 43.660 | 3.0 |
| 2.039 | 44.427 | 0.3 |
| 1.977 | 45.880 | 11.4 |
| 1.950 | 46.568 | 4.4 |
| 1.932 | 47.030 | 3.9 |
| 1.915 | 47.476 | 3.7 |
| 1.838 | 49.594 | 6.4 |
| 1.835 | 49.667 | 5.5 |

TABLE 4

| | | | | | COMPOSITION | | | |
|---|---|---|---|---|---|---|---|---|
| Example | $\frac{\text{Moles C}}{\text{Mole N}}$ | Moles per Mole Al$_2$O$_3$ | | | $\frac{Al}{100T_d}$ | $\frac{Na^+}{100T_d}$ | $\frac{N^+}{100T_d}$ | $\frac{R}{100T_d}$ |
| | | N$_2$O | Na$_2$O | SiO$_2$ | | | | |
| 1 | 9.5 | 4.09 | 0.85 | 223 | 0.89 | 0.76 | 3.6 | 3.8 |
| 2 | 11.2 | 2.43 | 0.74 | 140 | 1.4 | 1.0 | 3.4 | 4.2 |
| 3 | 9.6 | 1.85 | 0.13 | 83 | 2.4 | 0.30 | 4.4 | 4.7 |
| 4 | 10.2 | 1.69 | 0.12 | 78 | 2.5 | 0.30 | 4.2 | 4.8 |
| 5 | 10.8 | 1.77 | 0.25 | 85 | 2.3 | 0.58 | 4.1 | 4.9 |
| 6 | 9.6 | 1.50 | 0.10 | 62 | 3.1 | 0.30 | 4.7 | 5.0 |

EXAMPLE 7

A sample of the Example 4 product crystals, having been calcined in nitrogen for 4 hours at 500° C., ammonium exchanged and then converted to the hydrogen form, was subjected to the sorption test. Significant n-hexane, i.e. 8 weight percent at 90° C., was sorbed while only minimal cyclohexane (about 1 weight percent at 90° C.) was sorbed. This indicates molecular shape selectivity for the ZSM-58.

EXAMPLE 8

The sample of Example 4 product used for sorption evaluation was evaluated in the Alpha Test. Its Alpha Value proved to be 13 at 538° C.

EXAMPLE 9

To demonstrate the present invention, propylene feedstock was pased over hydrogen-form ZSM-58 prepared as in Example 7 at conversion conditions including atmospheric pressure (101.325 kPa), 300° C. and 5.3 $hr^{-1}$ liquid hourly space velocity. At 52% conversion, the product distribution was as shown in Table 5.

TABLE 5

| Product Hydrocarbon | Wt. % |
|---|---|
| Methane | 0.1 |
| Ethane | 0.1 |
| Ethylene | 0.2 |
| Propane | 2.4 |
| Propylene | — |
| i-Butane | 3.7 |
| n-Butane | 0.1 |
| Butenes | 18.6 |
| $C_5$ Olefins | 5.8 |
| $C_6$ Olefins | 17.0 |
| $C_7$ Olefins | 19.1 |
| $C_8$ Olefins | 22.1 |
| $C_9$ Olefins | 9.3 |
| $C_{10}^+$ Olefins | 1.5 |

EXAMPLE 10

To further demonstrate the present invention, a 2 gram sample of calcined product from Example 7 is placed in a reactor vessel and contracted with feedstock comprised of propylene at 230° C., 10,339 kPa and 0.38 $hr^{-1}$ (LHSV). Conversion of propylene is measured to be about 55 wt. % with the product comprised of about 45% 30°–330° F. b.p. material, 53% 330°–650° F. b.p. material and 2% 650° F.+ b.p. material.

EXAMPLE 11

A feedstock of one-half propane and one-half butane is passed through the reactor vessel containing 2 grams of freshly calcined product from Example 7 at a temperature of 500° C., a pressure of 1000 kPa and a liquid hourly space velocity of 5 $hr^{-1}$. Product comprising benzene, toluene and xylenes is observed with conversion of feedstock paraffins measured at about 50%.

What is claimed is:

1. A process for converting a feedstock comprising $C_2^+$ olefins, $C_2$–$C_7$ paraffins or mixtures thereof to conversion product $C_5^+$ hydrocarbon compounds, which comprises contacting said feedstock at conversion conditions sufficient to convert said feedstock to said product with a catalyst composition comprising a crystalline zeolite characterized by an X-ray diffraction pattern exhibiting values substantially as set forth in Table 1 of the specification, said zeolite when in the as-synthesized form having a formula, on an anhydrous basis and in terms of moles of oxides per 100 moles of silica, as follows:

$$(0.1–2.0)R_2O:(0.02–1.0)M_{2/n}O:(0.1–2)Al_2O_3:(100-)SiO_2$$

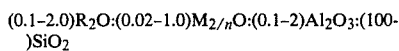

wherein M is an alkali or alkaline earth metal cation, n is the valence of M, and R is an organic cation.

2. The process of claim 1 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

3. The process of claim 2 wherein said replacing cations are hydrogen or hydrogen precursor.

4. The process of claim 1 wherein said catalyst composition comprises said zeolite and a matrix.

5. The process of claim 2 wherein said catalyst composition comprises said zeolite and a matrix.

6. The process of claim 4 wherein said matrix is alumina-containing material.

7. The process of claim 5 wherein said matrix is alumina-containing material.

8. The process of claim 4 wherein said catalyst composition is in the form of an extrudate.

9. The process of claim 4 wherein said catalyst composition is in the form of beads.

10. The process of claim 1 wherein said conversion conditions include a temperature of from about 100° C. to about 700° C., a pressure of from about 10 kPa to about 11,000 kPa, a liquid hourly space velocity of from about 0.1 $hr^{-1}$ to about 500 $hr^{-1}$ and a hydrogen/hydrocarbon mole ratio of from 0 to about 20.

11. A process for converting a feedstock comprising $C_2$–$C_7$ olefins to conversion product $C_5^+$ hydrocarbon compounds, which comprises contacting said feedstock at conversion conditions sufficient to convert said feedstock to said product with a catalyst composition comprising a crystalline zeolite characterized by an X-ray diffraction pattern exhibiting values substantially as set forth in Table 1 of the specification, said zeolite when in the as-synthesized form having a formula, on an anhydrous basis and in terms of moles of oxides per 100 moles of silica, as follows:

$$(0.1–2.0)R_2O:(0.02–1.0)M_{2/n}O:(0.1–2)Al_2O_3:(100-)SiO_2$$

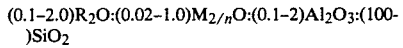

wherein M is an alkali or alkaline earth metal cation, n is the valence of M, and R is an organic cation.

12. The process of claim 11 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

13. The process of claim 12 wherein said replacing cations are hydrogen or hydrogen precursor.

14. The process of claim 11 wherein said catalyst composition comprises said zeolite and a matrix.

15. The process of claim 14 wherein said matrix is alumina-containing material.

16. The process of claim 11 wherein said conversion conditions include a temperature of from about 190° C. to about 375° C., a pressure of from about 400 kPa to about 11,000 kPa and a liquid hourly space velocity of from about 0.3 $hr^{-1}$ to about 2 $hr^{-1}$.

17. The process of claim 16 wherein said conversion conditions include a temperature of from about 190° C. to about 315° C., a pressure of from about 4200 kPa to about 11,000 kPa and a liquid hourly space velocity of from about 0.3 $hr^{-1}$ to about 1 $hr^{-1}$.

18. The process of claim 16 wherein said conversion conditions include a temperature of from about 230° C. to about 375° C., a pressure of from about 400 kPa to about 4700 kPa and a liquid hourly space velocity of from about 0.3 hr$^{-1}$ to about 2 hr$^{-1}$.

19. The process of claim 1 wherein said zeolite has been thermally treated at a temperature up to about 925° C.

20. The process of claim 2 wherein said treated zeolite has been thermally treated at a temperature up to about 925° C.

21. The process of claim 11 wherein said zeolite has been thermally treated at a temperature up to about 925° C.

22. The process of claim 12 wherein said treated zeolite has been thermally treated at a temperature up to about 925° C.

23. A process for converting a feedstock comprising $C_2+$ olefins, $C_2$–$C_7$ paraffins or mixtures thereof to conversion product comprising $C_5+$ hydrocarbon compounds, which comprises contacting said feedstock at conversion conditions sufficient to convert said feedstock to said product with a catalyst composition comprising ZSM-58.

24. A process for converting a feedstock comprising $C_2$–$C_7$ olefins to conversion product comprising $C_5+$ hydrocarbon compounds, which comprises contacting said feedstock at conversion conditions sufficient to convert said feedstock to said product with a catalyst composition comprising ZSM-58.

* * * * *

UNITED STATES PATENT AND TRADEMARK OFFICE
CERTIFICATE OF CORRECTION

PATENT NO. : 4,665,264
DATED : May 12, 1987
INVENTOR(S) : Paul G. Rodewald et al It is certified that error appears in the above-identified patent and that said Letters Patent is hereby corrected as shown below:

Col. 1, line 44, "cationl." should be --cation.--
Col. 3, line 12, "4,456,778" should be --4,456,779--
Col. 9, line 13, "pased" should be --passed--

Signed and Sealed this

First Day of September, 1987

Attest:

DONALD J. QUIGG

Attesting Officer      Commissioner of Patents and Trademarks